US00PP21181P3

(12) United States Plant Patent
Álamo et al.

(10) Patent No.: US PP21,181 P3
(45) Date of Patent: Aug. 3, 2010

(54) BLUEBERRY PLANT NAMED 'AZULEMA'
(50) Latin Name: ***Vaccinium corymbosum* L.**
Varietal Denomination: Azulema

(75) Inventors: Antonio Abad Álamo, Huelva (ES); José Ulf Hayler López, Huelva (ES); Paul M. Lyrene, Micanopy, FL (US)

(73) Assignee: Royal Berries S.L., Almonte, Huelva (ES)

( * ) Notice: Subject to any disclaimer, the term of this patent is extended or adjusted under 35 U.S.C. 154(b) by 0 days.

(21) Appl. No.: 12/289,127

(22) Filed: Oct. 21, 2008

(65) Prior Publication Data

US 2009/0210981 P1 Aug. 20, 2009

(30) Foreign Application Priority Data

Feb. 14, 2008 (QZ) ..... PBR 2008/0345

(51) Int. Cl.
*A01H 5/00* (2006.01)

(52) U.S. Cl. ..... Plt./157

(58) Field of Classification Search ..... Plt./57
See application file for complete search history.

*Primary Examiner*—June Hwu
(74) *Attorney, Agent, or Firm*—Buchanan Ingersoll & Rooney PC

(57) ABSTRACT

A new and distinct Blueberry cultivar is provided that is the product of a controlled breeding program followed by selection. The cultivar flowers and forms fruit at mid-season. The attractive high quality firm light blue flattened-round berries exhibit a superb aromatic blueberry flavor. The plant is self-fertile, and displays a generally round to vase-shaped growth habit with attractive evergreen foliage. A low chilling requirement is also exhibited.

6 Drawing Sheets

Botanical/commercial classification: *Vaccinium corymbosum* L./Blueberry Plant.

Varietal denomination: cv. Azulema.

SUMMARY OF THE INVENTION

The new Blueberry cultivar of the present invention was the product of controlled artificial pollination carried out in a greenhouse at Greenwood, Fla., U.S.A., wherein two parents were crossed during 1998 which previously had been studied in the hope that they would contribute the desired characteristics. The female parent (i.e., the seed parent) was the unreleased 'FL 90-4' cultivar (non-patented in the United States). The male parent (i.e., pollen parent) was the unreleased 'FL 96-32' cultivar (non-patented in the United States). The parentage of the new cultivar can be summarized as follows:

'FL 90-4'×'FL 96-32'.

The seeds resulting from the pollination were shipped to Almonte, Huelva, Spain, where they sown during approximately 2000, small plants were obtained which were physically and biologically different from each other and selective research of the progeny was carried out. Selective study during the spring of 2003 resulted in the identification of a single plant of the new cultivar. This plant initially was designated S03-38-01.

It was found that the new Blueberry plant of the present invention displays the following combination of characteristics:

(a) flowers and forms fruit at mid-season,
(b) displays a generally round to vase-shaped growth habit with attractive evergreen foliage,
(c) is self-fertile,
(d) displays a low chilling requirement, and
(e) forms in abundance attractive firm light blue flattened-round berries that exhibit a superb aromatic blueberry flavor and a good shelf life following harvest.

The new cultivar well meets the needs of the horticultural industry and can be grown to advantage for the commercial production of blueberries. It is recommended that the plant be grown under tunnels in warm areas with well drained soils while using evergreen management procedures.

The new cultivar of the present invention can be distinguished from all available Blueberry cultivars known to its originators. Each parent plant is unreleased to the public. No comparative information is available concerning the distinguishing characteristics of the new cultivar when compared to the 'FL 90-4' and 'FL 96-32' parental cultivars. Also, since the parental cultivars no longer exist, it is impossible to obtain such comparative information. When compared to the Star cultivar (U.S. Plant Pat. No. 10,675), the 'Star' cultivar commonly displays a taller, more upright growth habit. When compared to the 'Millenia' cultivar (U.S. Plant Pat. No. 12,816), the 'Millenia' cultivar commonly requires cross-pollination unlike the new cultivar of the present invention. When compared to the 'O'Neal' cultivar (non-patented in the United States), the 'O'Neal' cultivar lacks an evergreen winter stage and forms darker blue berries and requires a longer chill requirement of approximately 500 hours. The new cultivar is less susceptible to Leaf Rust than the 'Blue Crisp' cultivar (U.S. Plant Pat. No. 11,033), and is more resistant to Stem Blight than the 'Biloxi' cultivar (non-patented in the United States).

The new cultivar has been asexually reproduced by the rooting of softwood cuttings beginning during the summer of 2003 at Almonte, Huelva, Spain. Such asexual propagation has shown that the characteristics of the new cultivar are firmly fixed and are stably transmitted from one generation to another. Accordingly, the new cultivar asexually reproduces in a true to type manner.

The new cultivar has been named 'Azulema'.

BRIEF DESCRIPTION OF THE PHOTOGRAPHS

The accompanying photographs show in color as nearly true as it is reasonably possible to make the same in color illustrations of this character, typical plants and plant parts of the new cultivar. The plants which had been asexually reproduced by the rooting of softwood cuttings, and were being grown outdoors at Almonte, Huelva, Spain.

DETAILED DESCRIPTION

Figure 1:
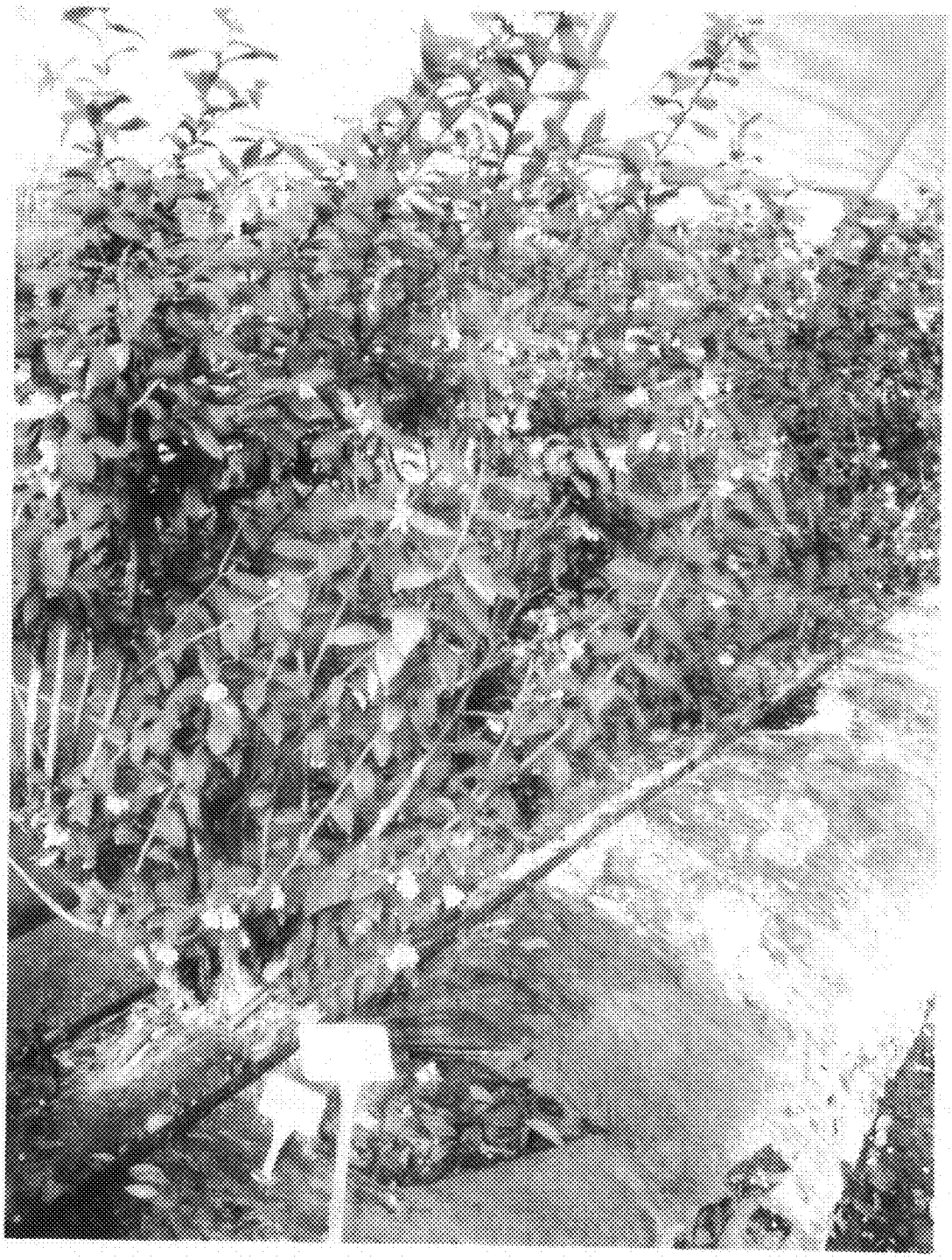
FIG. 1 shows an overall view of a typical flowering plant of the new cultivar where the generally round to vase-shaped growth habit is illustrated.
Figure 2:
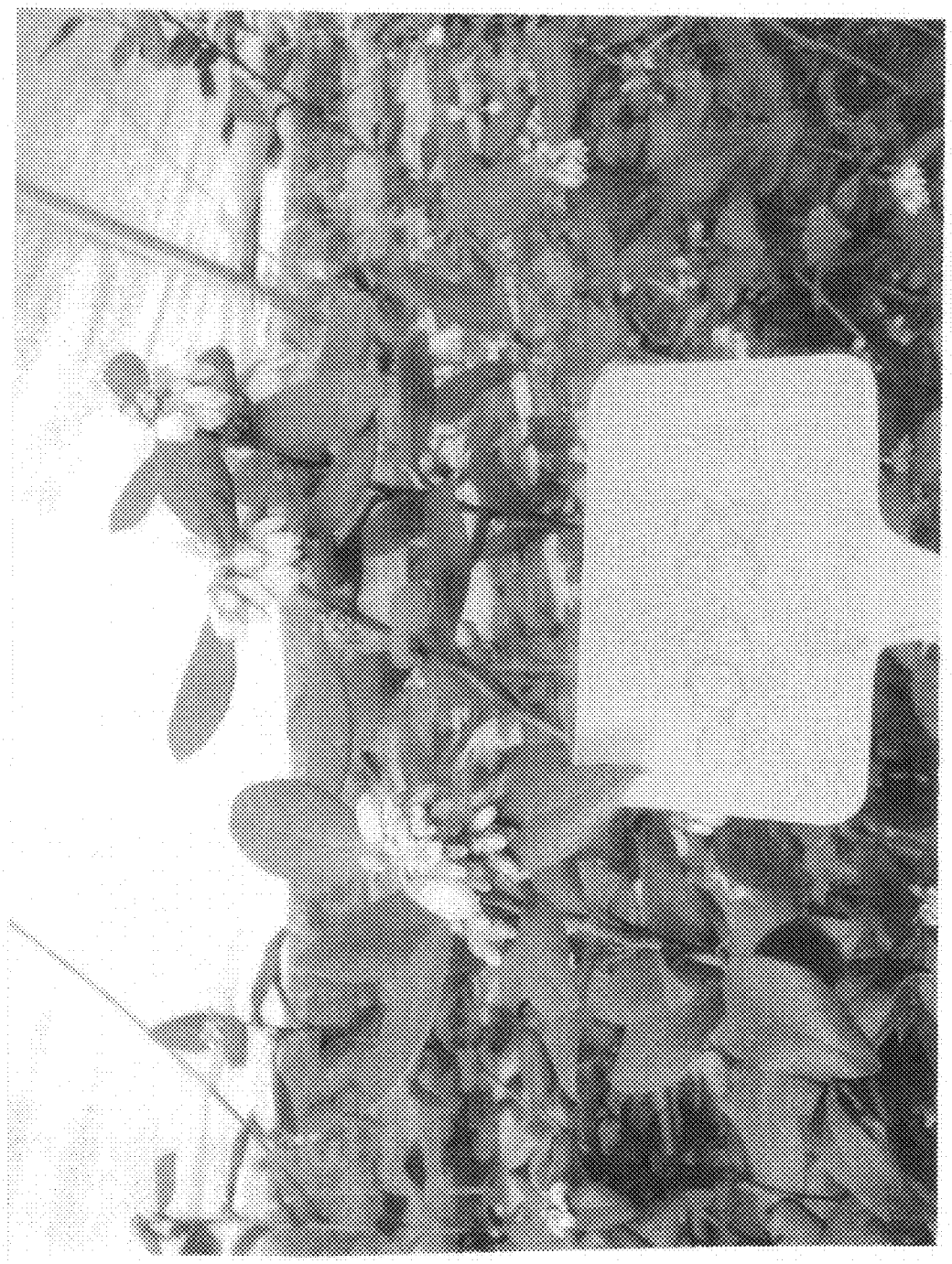
FIG. 2 shows a close view of typical flowers of the new cultivar.
Figure 3:
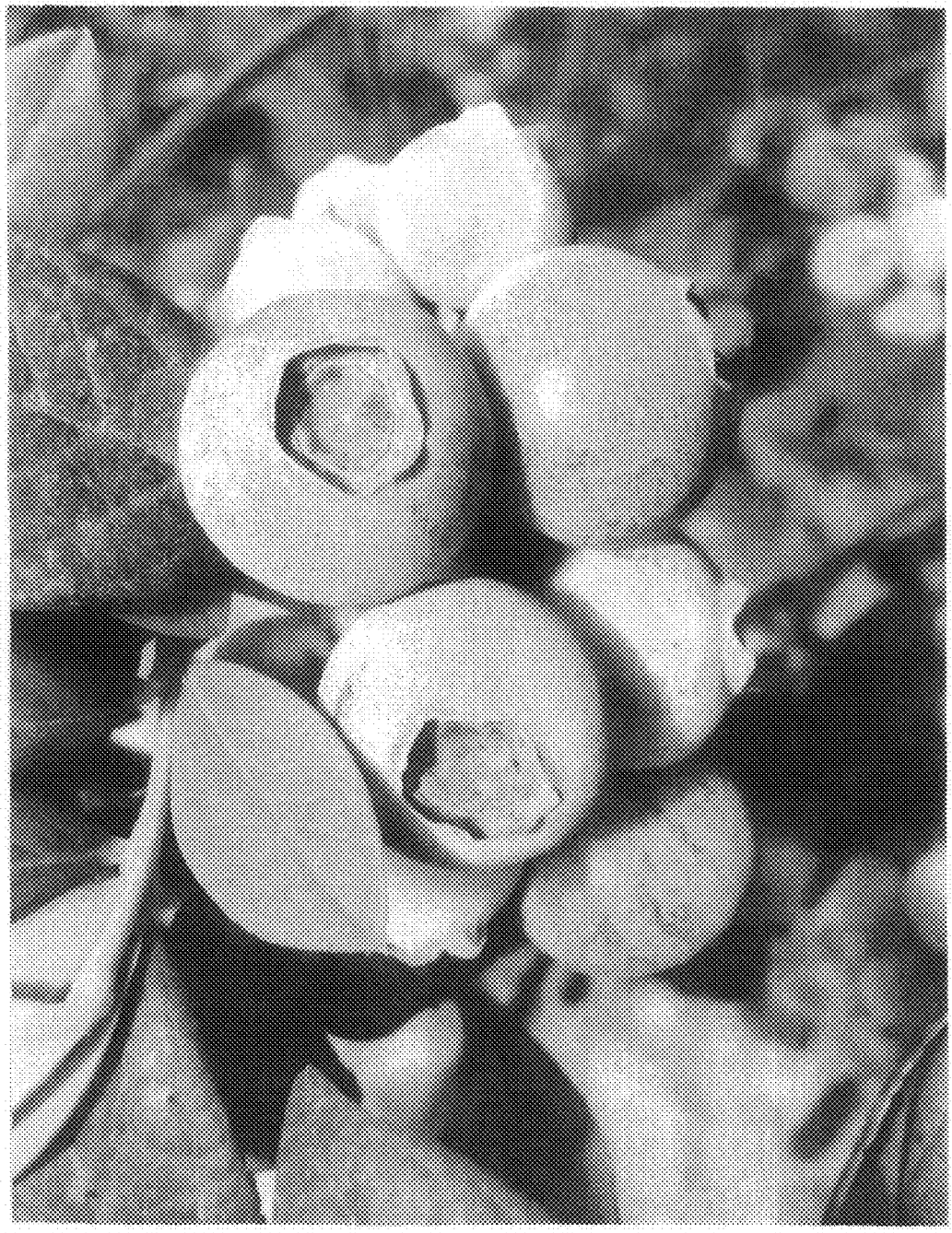
FIG. 3 shows a cluster of typical berries in various stages of development and the foliage of the new variety.
Figure 4:
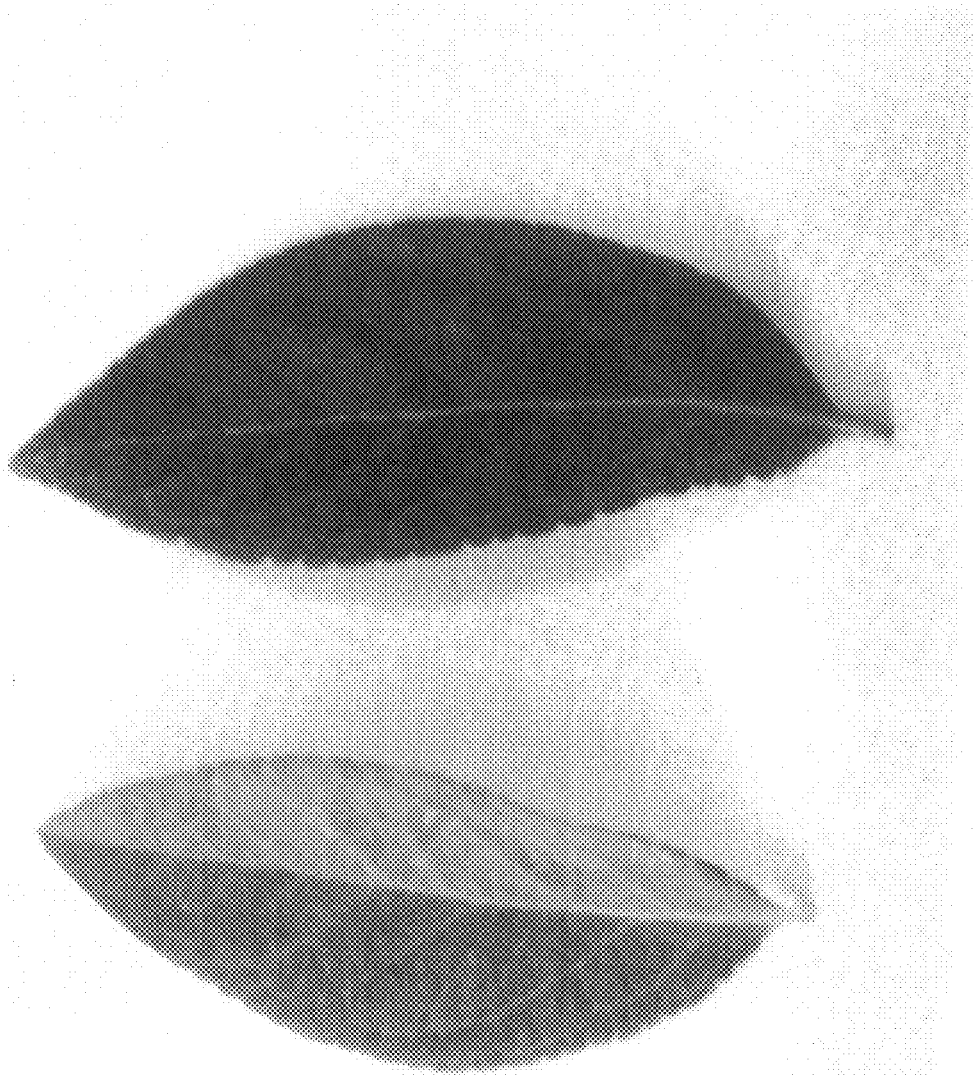
FIG. 4 shows upper (adaxial) surfaces of typical leaves of the new cultivar.
Figure 5:
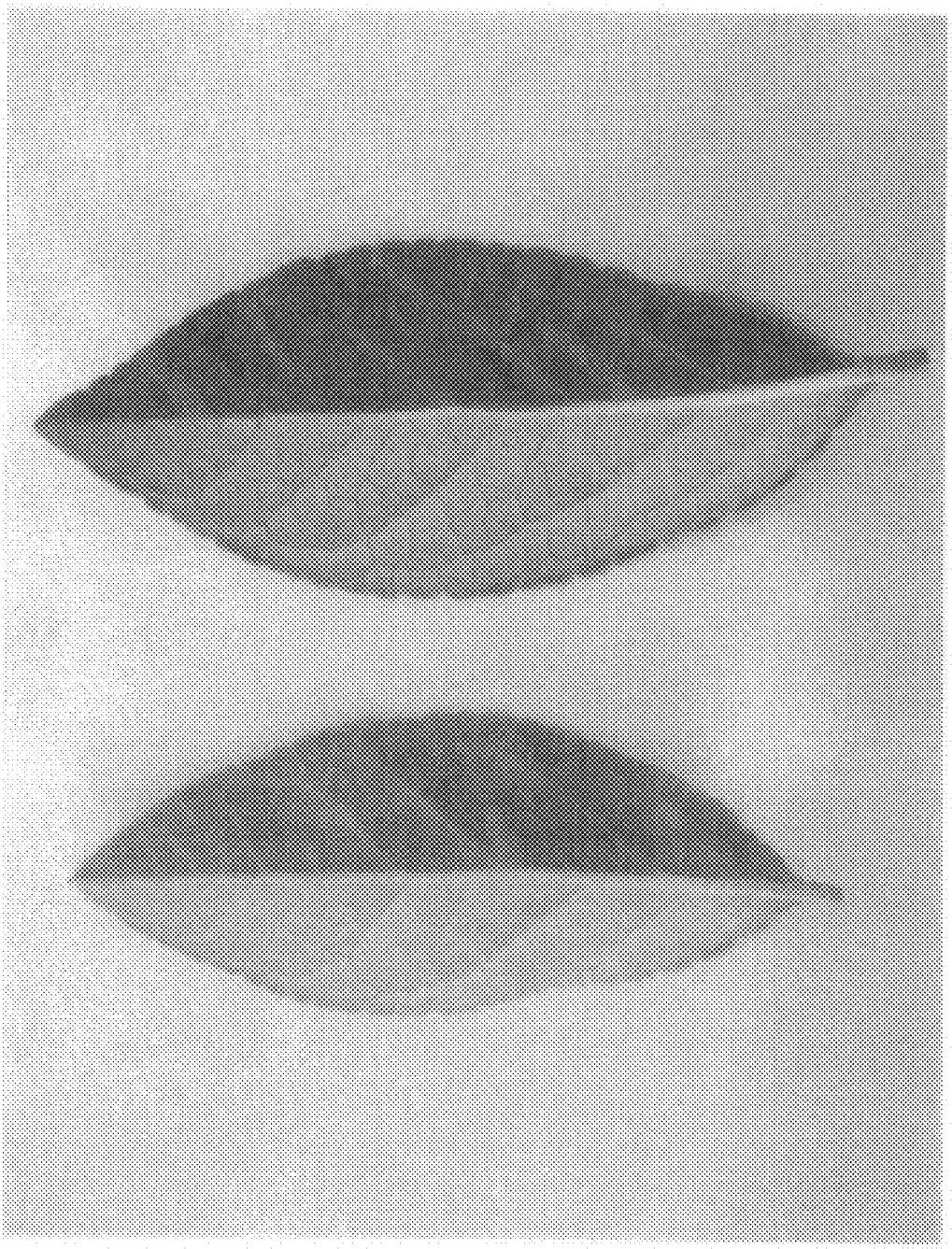
FIG. 5 shows under (abaxial) surfaces of typical leaves of the new cultivar.
Figure 6:
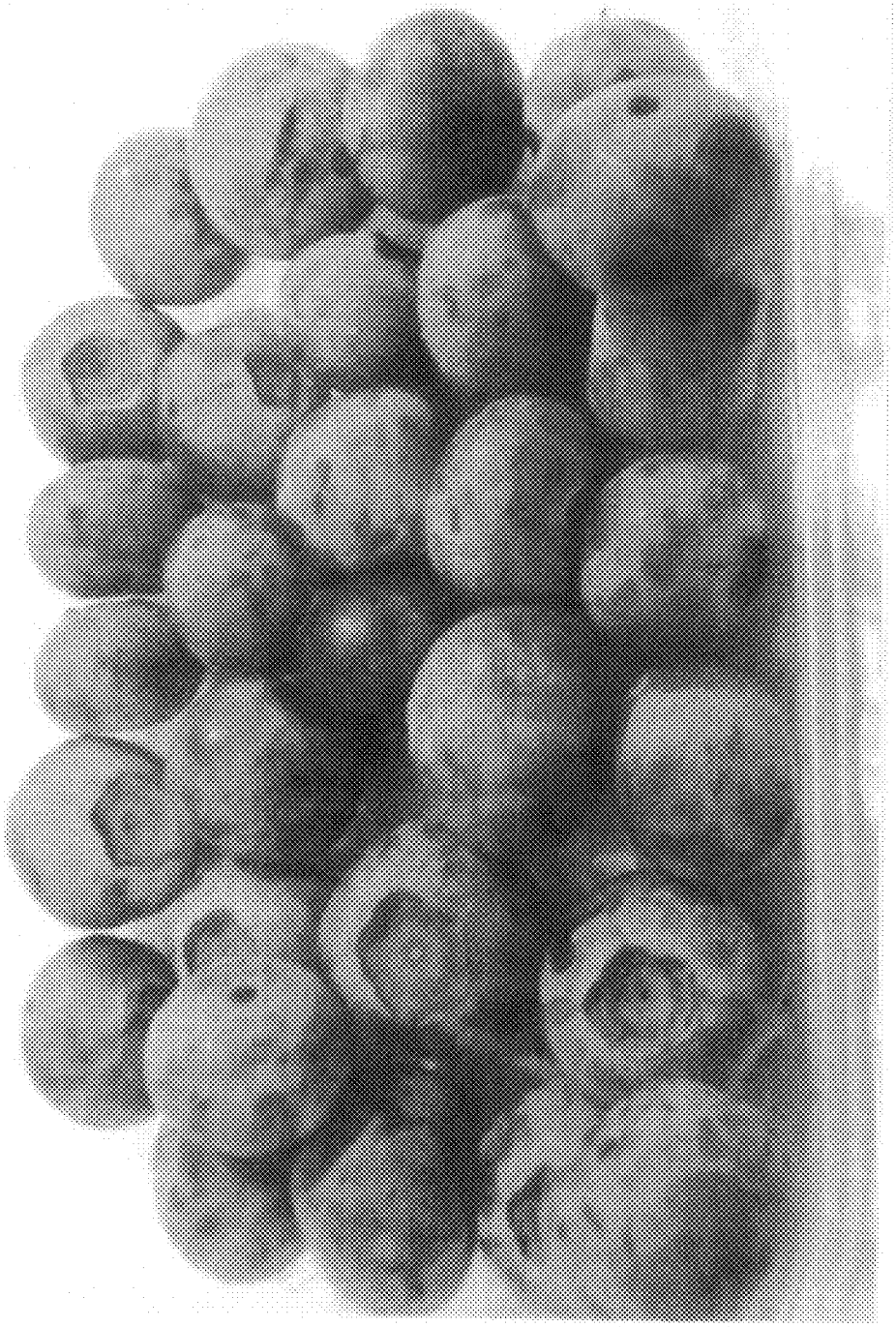
FIG. 6 shows a close view of an array of typical mature berries of the new cultivar.

The chart used in the identification of the colors described herein is The R.H.S. Colour Chart of The Royal Horticultural Society, London, England. Ordinary color terms are to be accorded their customary dictionary significance. The description is based on the observation of approximately four-year-old plants of the new cultivar which had been asexually reproduced by the rooting of softwood cuttings while growing outdoors at Almonte, Huelva, Spain.

Plant:

*Growth habit.*—Generally round to vase-shaped.

*Height.*—Approximately 1.4 m at 4 years of age.

*Width.*—Approximately 3.3 m at 4 years of age.

*Mature canes.*—Commonly approximately 38.3 cm in length on average, approximately 2.4 cm in diameter at the base on average, approximately 1.7 cm in diameter towards the tip; and near Grey-Brown Group 199D in coloration.

*Foliage retention.*—Evergreen.

*Chill requirement.*—Commonly less than approximately 300 hours.

Foliage:

*Shape.*—Narrowly elliptic (as illustrated).

*Length.*—Commonly approximately 67 mm on average.

*Width.*—Commonly approximately 33 mm on average.

*Apex.*—Acute.

*Base.*—Acute.

*Margin.*—Crenate.

*Texture.*—Glabrous and non-glandular on both surfaces.

*Color.*—Green Group 137B on the upper (adaxial) surface, and Green Group 138C on the under (abaxial) surface.

*Petiole.*—Commonly approximately 3.6 mm in length on average, commonly approximately 1.7 mm in diameter on average, and the coloration is near Yellow-Green Group 144C on both surfaces.

Flowers:

*Time.*—Mid-season, at Almonte, Huelva, Spain, with first flower commonly at approximately December 20$^{th}$, and 50 percent bloom at approximately February 20$^{th}$.

*Number.*—Commonly approximately 7 flowers per inflorescence on average.

*Petals.*—5 in number and fused into a corolla tube.

*Corolla shape.*—Urceolate.

*Corolla size.*—The corolla tube commonly is approximately 9.1 mm in length on average, and approximately 7.8 mm in width on average at the widest point.

*Corolla color.*—Commonly near Green-White Group 157D.

*Sepals.*—Commonly 5 in number.

*Calyx.*—Commonly approximately 2.6 mm in length on average, a basin depth of approximately 1.9 mm, a basin diameter of approximately 7.1 mm, and a coloration of Green Group 142A and 142B.

*Filaments.*—Commonly adnate at the base and strongly connected to the petals, pale green in coloration, and approximately 4.2 mm in length on average.

*Anthers.*—Bronze-colored, approximately 3 to 4 mm in size on average, and the size ratio of the pollen sac: pollen tube commonly varies from 1:1 to 2:3.

*Pistil.*—One per flower and light green in coloration.

*Style.*—Cone-shaped in configuration, approximately 8.2 mm in length on average, and approximately 0.7 to 0.9 mm in thickness at the base on average.

*Peduncle.*—Commonly approximately 3.9 mm in length, approximately 1.1 mm in width, and the coloration is near Green Group 149C.

*Fertility.*—Self-fertile.

*Fragrance.*—None.

Fruit:

*Time.*—Commonly from approximately April 7$^{th}$ to June 15$^{th}$ at Almonte, Huelva, Spain (i.e., approximately 8 weeks).

*Shape.*—Generally flattened-round.

*Height.*—Commonly approximately 15 mm on average.

*Width.*—Commonly approximately 18 mm on average.

*Weight.*—Approximately 2.65 g/berry on average when plants were 4 years of age.

*Fruit scar.*—Approximately 1.2 mm in size, dry, and relatively deep (as illustrated).

*Seed number.*—Commonly approximately 20 per berry on average.

*Seed size.*—Commonly approximately 1.4 mm in length and approximately 0.9 mm in width on average.

*Immature color.*—Commonly near Green Group 142D with bloom, and Yellow-Green Group 145A without bloom.

*Mature color.*—Light blue, Violet Blue Group 97B to 97C with bloom, and Black Group 202A without bloom.

*Flesh color.*—Yellow Group 4D.

*Firmness.*—Medium.

*Productivity.*—Abundant, approximately 3.73 Kg/plant on average when plants are 4 years of age.

*Flavor.*—Displays a superb aromatic blueberry flavor, a typical acidity of approximately 0.62 g/100 g, and commonly displays a level of sweetness of approximately 14.0° Brix.

Development:

*Ability to store.*—The fruit stores well under refrigeration, when stored at 8° C. approximately 96 percent of the berries are of good quality 7 days after harvest, and when stored at 20° C. approximately 94 percent of the berries are of good quality 7 days after harvest.

*Disease tolerance.*—No special sensitivity to common Blueberry diseases. such as Leaf Rust (*Pucciniastrum vaccinii*) and *Botrytis* (*Botrytis cinerea*) has been encountered during observations to date at Almonte, Huelva, Spain. During observations to date the new cultivar is less susceptible to Leaf Rust than the 'Blue Crisp' cultivar, and is more resistant to Stem Blight than the 'Biloxi' cultivar.

*Insects.*—Is susceptible to aphids and thrips.

*Cultural conditions.*—Is well suited for evergreen management under tunnels.

*Heat resistance.*—Heat tolerant, has withstood temperature as high as 45° C. at Almonte, Huelva, Spain.

*Cold resistance.*—Has withstood temperature as low as −10° C. at Almonte, Huelva. Spain.

Plants of the 'Azulema' cultivar have not been observed under all possible environmental conditions to date, Accordingly, it is possible that the phenotypic expression may vary somewhat with changes in light intensity and duration, cultural practices, and other environmental conditions without variance in the genotype.

We claim:

1. A new and distinct Blueberry plant that possesses the following combination of characteristics:

(a) flowers and forms fruit at mid-season, (b) displays a generally round to vase-shaped growth habit with attractive evergreen foliage, (c) is self-fertile, (d) displays a low chilling requirement, and (e) forms in abundance attractive firm light blue flattened-round berries that exhibit a superb aromatic blueberry flavor and a good shelf life following harvest;

substantially as herein shown and described.

* * * * *